United States Patent [19]
Fishman et al.

[11] Patent Number: 5,816,255
[45] Date of Patent: Oct. 6, 1998

[54] METHOD FOR MAKING A CUSTOM MOUTH GUARD AND APPARATUS FOR DOING SAME

[75] Inventors: Laurence Fishman, Marina del Rey; Tony Stearns, Los Angeles; Sam Zadori, Burbank, all of Calif.

[73] Assignee: Trident Dental Laboratories, Inc., Marina Del Rey, Calif.

[21] Appl. No.: 585,720

[22] Filed: Jan. 16, 1996

[51] Int. Cl.$^6$ ..................................................... A61C 5/14
[52] U.S. Cl. ............................................ 128/861; 128/862
[58] Field of Search ........................... 128/848, 859–862; 2/2; 433/6

[56] References Cited

U.S. PATENT DOCUMENTS

| | | | |
|---|---|---|---|
| 2,706,478 | 4/1955 | Porter | 128/136 |
| 2,827,899 | 3/1958 | Altieri | 128/136 |
| 2,919,693 | 1/1960 | Ross | 128/136 |
| 3,124,129 | 3/1964 | Grossberg | 128/136 |
| 3,224,443 | 12/1965 | Monaghan | 128/136 |
| 3,250,272 | 5/1966 | Greenberg | 128/136 |
| 3,310,521 | 3/1967 | White et al. | 260/37 |
| 3,379,193 | 4/1968 | Monaghan | 128/136 |
| 3,411,501 | 11/1968 | Greenberg | 128/136 |
| 4,063,552 | 12/1977 | Going et al. | 128/136 |
| 4,569,342 | 2/1986 | Von Nostitz | 128/136 |
| 5,031,638 | 7/1991 | Castalidi | 128/861 |
| 5,152,301 | 10/1992 | Kittelsen et al. | 128/861 |
| 5,320,114 | 6/1994 | Kittlelsen | 128/861 |
| 5,365,946 | 11/1994 | McMillan | 128/862 |
| 5,406,962 | 4/1995 | Adell | 128/861 |
| 5,562,106 | 10/1996 | Heeke | 128/861 |

*Primary Examiner*—Michael A. Brown
*Attorney, Agent, or Firm*—Cislo & Thomas

[57] ABSTRACT

A method for forming a mouth guard and apparatus for anatomically conforming the impression material to a user's mouth and teeth. Polyvinyl siloxane base putty is combined in equal parts with polyvinyl siloxane catalyst putty until a uniform amalgam is formed by kneading and mixing. The mass is then formed into a roll of about three inches in length having a thicker center and extended and tapering ends with a one-inch diameter at the center and approximately half-inch diameters at the ends. A bite bar having a lateral handle is pressed through the center of the mass to form grasping means by which the putty-mass-and-bite-bar, or mouth-guard, assembly may be easily handled. A shield (that may have prongs) on the bite bar serves to support and obstruct the passage of the putty mass. Curving the putty mass about the shield and optional prongs serves to conform the putty mass to the anatomical curvature of a user's teeth. The assembly is placed into the mouth with the handle extending centrally from the user's mouth. The user then bites into the putty mass for approximately three to five minutes while the putty sets. An exact mold of the user's teeth is then created in the putty mass. When the putty has sufficiently set, the assembly is then removed from the user's mouth. The bite bar is then removed from the mass, leaving an aperture through which the user may breathe while holding the mouth guard between the teeth. Extraneous material may be cut from the mouth guard, and the mouth guard may be preserved in a closed box or tray for convenience.

25 Claims, 8 Drawing Sheets

METHOD FOR MAKING A CUSTOM MOUTH GUARD AND APPARATUS FOR DOING SAME

BACKGROUND OF THE INVENTION

1. Field of the Invention

The present invention relates to the making of mouth guards that closely fit the wearer's teeth and absorb shock in order to protect the teeth and, more particularly to a method for making a mouth piece that conforms in a plastic and exact manner to the dental configuration of a specific wearer.

2. Description of the Related Art

In sports and other activities where rough play is common, blows to a player's mouth may loosen, break, or knock entirely loose one or more teeth. Such sports include football and hockey. In football, mouthpieces are often used and commonly a required piece of equipment on the playing field. In hockey, the puck often flies free from the surface of the ice to strike one of the players in the mouth. It is not uncommon to see the grins of hockey players marked with one or more absent teeth. Other sports and activities may also prompt the use of a mouthpiece in order to protect the teeth.

Listed below are patents related to the art of the present invention.

| PATENT NUMBER | INVENTOR | ISSUE DATE |
| --- | --- | --- |
| 2,706,478 | Porter, M. M. | April 19, 1955 |
| 2,827,899 | Altieri, D. J. | March 25, 1958 |
| 2,919,693 | Ross, H. M. | January 5, 1960 |
| 3,124,129 | Grossberg, M. E. | March 10, 1964 |
| 3,224,443 | Monaghan, R. P. | December 21, 1965 |
| 3,250,272 | Greenberg, S. | May 10, 1966 |
| 3,310,521 | White, B. B., et al. | March 21, 1967 |
| 3,379,193 | Monaghan, R. P. | April 23, 1968 |
| 3,411,501 | Greenberg, S. | November 19, 1968 |
| 4,063,552 | Going, R. E., et al. | December 20, 1977 |
| 4,569,342 | von Nostiz, F. H. F. | February 11, 1986 |
| 5,031,638 | Castaldi, C. R. | July 16, 1991 |
| 5,121,301 | Kittelsen, J. D., et al. | October 6, 1992 |

A more in-depth description of the more pertinent patents follows below.

C. R. Castaldi, U.S. Pat. No. 5,031,638

This patent is directed to a direct-formed mouth guard and a method of making same. The mouth guard is made from a blank which comprises a material that is moldable, settable, and which conforms to a user's intra-oral structures when subjected to bite pressure. The preferred thermoplastic material used is a copolymer of ethylene and vinyl acetate. The blank 10 is seen in FIG. 1 and is formed into a generally arcuately shaped structure to fit over either the upper or lower row of teeth. The blank is first prefitted to the user's mouth by heating the material and shaping it to conform to the general shape of the oral cavity of the user. The blank is then cooled and re-immersed in boiling water for one or two minutes so that the blank reaches a predetermined temperature range. The blank is then rinsed in room-temperature water and then quickly inserted into the user's mouth, and the user then bites down firmly on the blank to form the impressions of the intra-oral structures. The bite pressure is maintained for two or three minutes while the thermoplastic material sets. The blank is then removed from the mouth and immersed in cold water to fix the impressions and form the mouth guard.

R. E. Going, et al., U.S. Pat. No. 4,063,552

This reference describes a user-formed mouth guard which is made of a silicone material such as a high molecular weight polymer (dimethyl siloxane) with sufficient trialkoxy silane and/or tetralkoxy silane to cure the polymer. Referring to FIG. 4, the tray assembly comprising an outer portion 1 and an inner portion 2 is designed to receive a U-shaped sample of the material 26 which is used to form the mouth guard.

H. M. Ross, U.S. Pat. No. 2,919,693

This patent describes a mouthpiece which is formed to fit the individual who is to wear it. The guard is formed from a plastic silicone rubber to which is added a catalyst which allows the material to set in a short period of time. One example of a suitable plastic silicone to be used is methyl polysiloxane. The catalyst used is a tin octoate which gives the plastic silicone stock material a setting time of less than ten minutes. The mouth guard is formed to fit the exact shape of the teeth of the individual wearer, and no heat is required in the process since the plastic material is a polymerizable material instead of a thermoplastic material. The resultant product may be boiled in hot water in order to sterilize it, is able to withstand both hot and cold temperatures, and has an indefinite life because it does not become brittle and hard with age. As already mentioned, the setting time is less than ten minutes but may be varied as desired and can be adjusted to be in the neighborhood of two to five minutes.

R. P. Monaghan, U.S. Pat. No. 3,379,193

This patent describes the process of forming and using teeth covers and utilizes a roll-shaped material formed into a U-shaped structure as seen in FIGS. 2 and 3.

B. B. White et al., U.S. Pat. No. 3,310,521

This patent is directed to the composition of curable materials. The materials are generally organopolysiloxanes wherein the organo portion may be selected from a wide variety of radicals as suggested in Column 2, beginning at Line 35. In Column 2, beginning at Line 65, that the radicals may also include vinyl groups.

R. P. Monaghan, U.S. Pat. No. 3,224,443

This patent suggests a "kit" concept wherein the catalyst may be added from a dropper 20 and mixed with the material such as the silicone rubber or elastomer 10 with a spatula 16 as seen in FIG. 1. The materials utilized are mainly plastic methyl polysiloxane to which the hardening agent 12 (catalyst) is added.

S. Greenberg, U.S. Pat. No. 3,411,501

This patent is directed to a thermoplastic mouthpiece and method of making same. It shows the concept of a hole being formed in the outer flange 12 (FIG. 18) in order to hold a strap element 66.

While the inventions set forth in the patents listed above have some degree of merit, they do not encompass the convenience and utility of the present invention. Particularly, several of the previously known methods for making a mouthpiece require additional steps or elements that are advantageously not present in the present invention.

SUMMARY OF THE INVENTION

The present invention provides a method and apparatus for creating a mouthpiece. The mouthpiece is held between the teeth and serves to prevent injury to the teeth by blows or other shocks inflicted thereon.

As indicated by the patents cited above, polyvinyl siloxane is a known substance with pliable characteristics that may be hardened into a resilient mass. Equal portions of approximately 7½ milliliters of a polyvinyl siloxane base putty is mixed with polyvinyl siloxane catalyst putty. The two putty masses are mixed together; and as the two putties generally have different color, equal mixing is generally considered to have taken place once the combined mass reaches a uniform color.

Upon thoroughly mixing the base and catalyst putties, the material is rolled into a generally tubular, or cylindrical, shape that is approximately three inches long with a one-inch diameter at the center and approximately a half-inch diameter at the ends. The bite bar is then pushed through the center of the cylindrical putty mass. The bite bar has a handle portion which projects through from the opposite side of the putty mass. The curved section of the bite bar serves to provide support for the putty mass as it is bent around the curved portion, the curved portion generally conforming to the interior geometry of an adult's mouth so as to fit between the occlusion surfaces of the teeth. The putty mass is then inserted into the mouth and bitten so as to impress the shape of the teeth into the mass while it hardens. Once the mass has been bitten into, the index or other finger is used to move and spread the putty material evenly around the teeth so that an impression of the person's entire dentistry is made.

After approximately three to five minutes, the putty mass is removed from the mouth; and the bite bar is pressed out of the material by pushing the handle towards the curved portion and holding the putty mass steady.

As the catalyst serves to harden the polyvinyl siloxane material, after approximately ten minutes the putty mass has hardened into a resilient form that serves as a mouth guard for an athlete engaging in rough sports. The hole left by the bite bar serves as a ventilation means so that a person using the mouth guard can breathe through the aperture formed by the bite bar.

OBJECTS OF THE INVENTION

It is an object of the present invention to provide a method for forming a mouth guard using polyvinyl siloxane or like materials.

It is an additional object of the present invention to provide a bite bar for use with polyvinyl siloxane impression materials so that the impression mass may be easily manipulated and also provide a breathing hole once the mass has hardened into a mouth piece.

It is another object of the present invention to provide a custom-fit mouth-guard system that can be used easily in the home without requiring a doctor's help while achieving a professional-quality mouthpiece.

These and other objects and advantages of the present invention will be apparent from a review of the following specification and accompanying drawings.

DESCRIPTION OF THE PREFERRED EMBODIMENTS

The present invention is directed to a method and means for forming a mouth guard that can protect the teeth from impact and blows. In the past, such mouth guards may not have been generally available. The invention further allows the use of a bite bar that provides handle means for the impression material and further provides an aperture through the front of the mouth guard so that breathing may take place through the wearer's mouth despite the presence of the mouth guard.

Figure 1A:
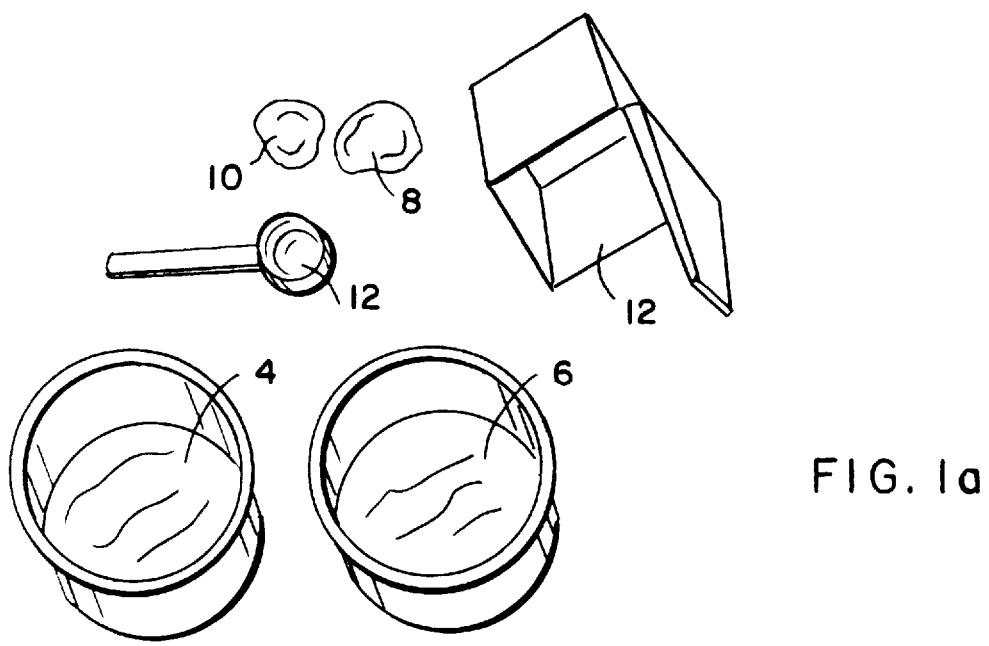
FIG. 1a shows in a top perspective view an assembly of the apparatus used to implement the present inventive method.

FIG. 1a shows the components comprising a kit version of the present invention. A scoop 2 is provided to collect amounts of base putty 4 and catalyst putty 6. As the putties are generally substantial and nonadhering in nature, they may be scooped out of a container containing the putties and set side by side so that equal volumes of base and catalyst putties 4, 6 are measured out. Such scoopfuls of putty are shown in FIG. 1a, indicated by reference numbers 8 for the base putty and 10 for the catalyst putty scoopfuls. In the present invention, the scoop contains approximately 7.5 milliliters of putty to ultimately comprise a viscous and self-hardening 15-milliliter mass. Once the mouth guard has been formed, it may be stored in a box or covered tray 12 that may be included with the kit.

Figure 1B:
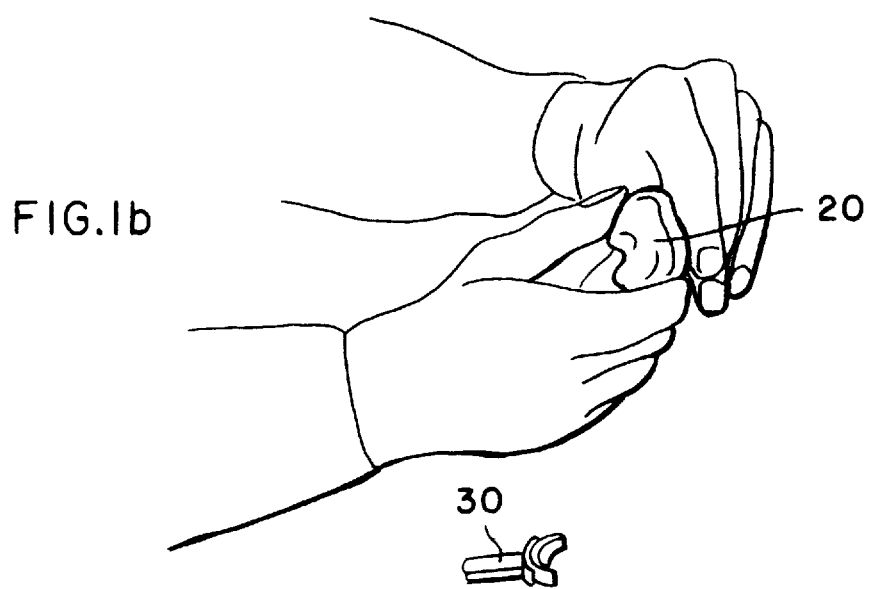
FIG. 1b shows in perspective view the manual mixing of base and catalyst putty materials and the bite bar of the present invention.
Figure 2:
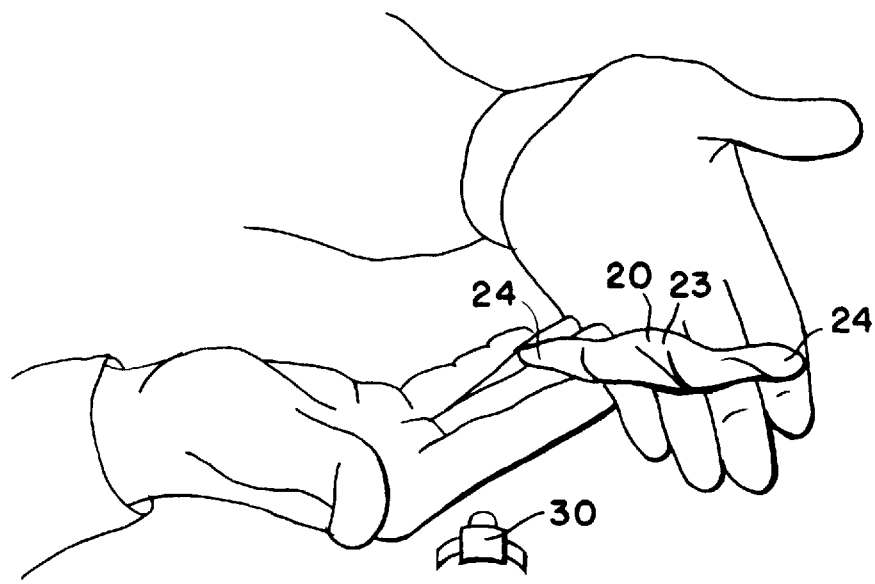
FIG. 2 shows a view of a thoroughly mixed putty mass ready for insertion of the bite bar.
Figure 3:
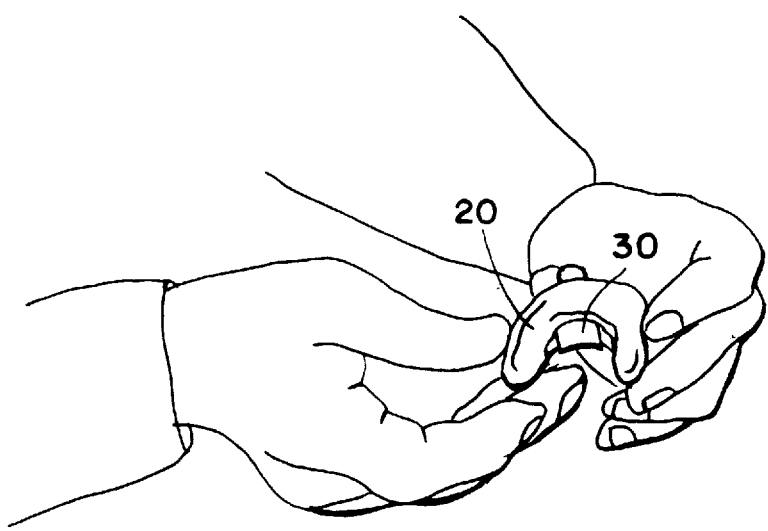
FIG. 3 shows the putty mass formed about the bite bar which has been inserted through the putty mass.

In FIG. 1b, the two scoopfuls of base and catalyst putty 8, 10 are manually mixed together to form an amalgam or solution of the putties. The resulting mass 20 initially has striations and variations of color; but as continual kneading and mixing takes place, the color becomes more uniform. Having the base putty a different color from the catalyst putty gives a visual indication of the thoroughness of the mixing process and is considered to be an advantageous feature. When the putty mass 20 has a uniform color, complete mixing is believed to be achieved.

Once thoroughly mixed, the amalgamated mass 20 should be rolled into a sausage-like shape having a thicker center with thinner ends. The mass should be approximately three inches long with a center diameter of approximately one inch tapering out to a half-inch diameter at its ends 24. Once the sausage-like shape has been attained by the thoroughly mixed putty mass 20, the bite bar 30 is pressed into the center 22 of the mass 20 until the handle 32 protrudes through the opposite end of the mass 20 and the shield 34

(FIG. 11) is resting against the mass 20. The two ends of the sausage-like shape 24 are then wrapped around the bite bar to curvedly engage the left and right prongs 36. 38 of the bite bar 30. The left and right prongs 36, 38 provide an advantageous curvature to the cylindrical putty mass 20 so that, once inserted in the mouth, the putty mass 20 will be between and obstruct the occluding surfaces of the teeth to provide material into which a dental impression can be made.

Figure 4:
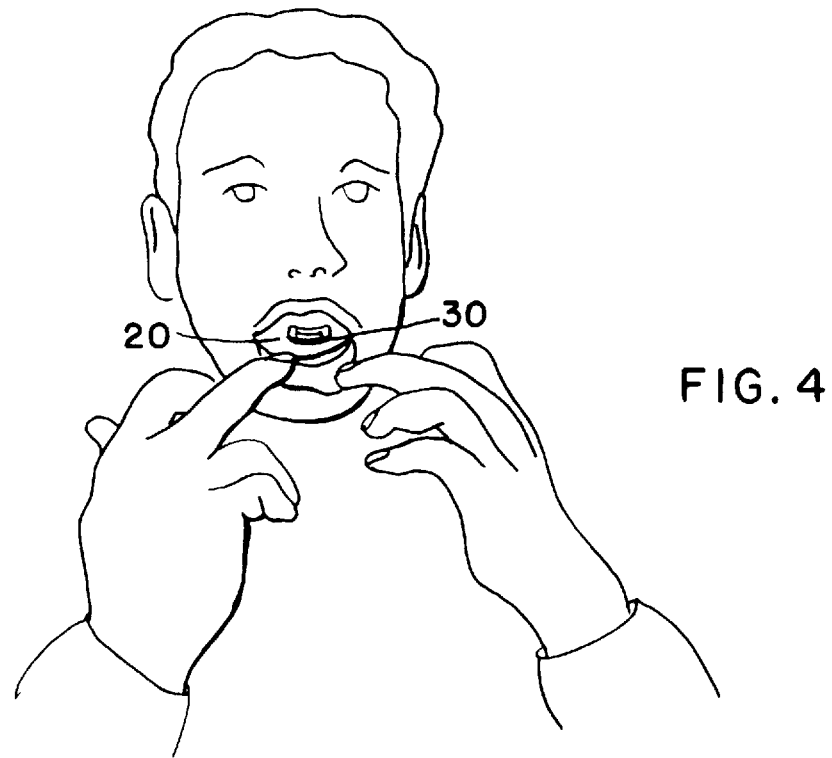
FIG. 4 shows the putty mass upon initial insertion into the mouth.

Once the bite bar 30 is appropriately situated into the putty mass 20 and the ends of the mass 24 are curved about the left and right prongs 36, 38, the putty mass with bite bar forms a mouth-guard assembly that is then inserted into the mouth between the jaws of the person for whom a mouth guard is to be fabricated. FIG. 4 shows an individual who has inserted the putty mass with bite bar into his mouth in between his teeth and has pulled down the lower lip to better show the mouth-guard assembly.

Figure 5:
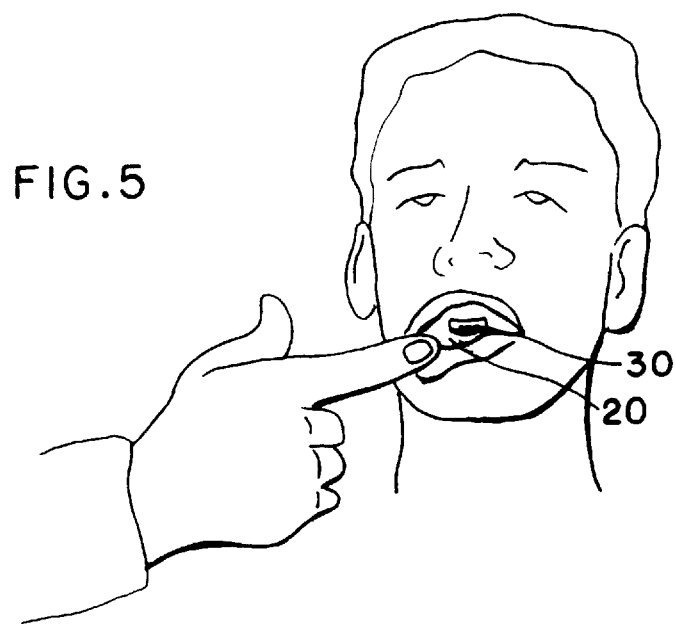
FIG. 5 shows the manual moving and spreading of the putty mass within the mouth.
Figure 6:
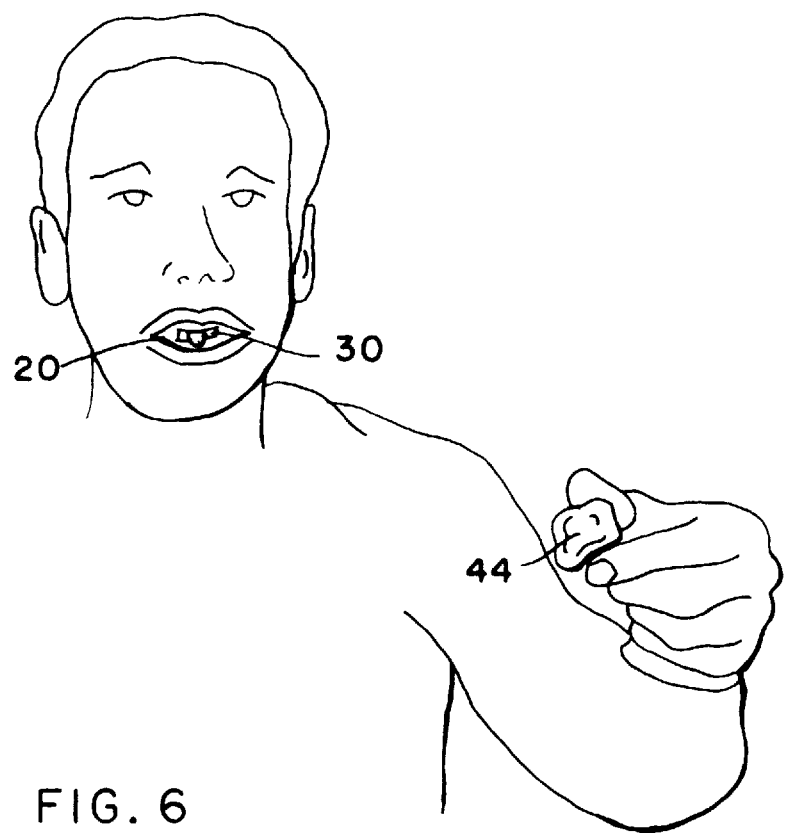
FIG. 6 shows a sample putty mass broken earlier from the mouth-inserted mass that can be used for testing readiness of the impressed mouth guard and to determine how the setting process is progressing.

As the putty is still soft at this point (although the catalytic reaction is continuing to take place to set the putty), the putty mass 20 may be spread with the fingers so as to engage the dental surfaces of the intended wearer. This is shown in FIG. 5, and the spreading or moving of the putty mass serves to create more surface area over which to distribute blows or other shocks to the mouth or jaw area.

When the mouth-guard assembly is inserted into the mouth, it is situated between the two jaws along the occluding surfaces of the teeth. The intended wearer of the mouth guard then bites into the putty mass so as to form the mouth guard. The resilient plastic and slow-flowing nature of the putty gives way to the pressure applied by the tooth surfaces. Even though the nontoxic putty flows slightly, it serves to provide an imprint of both upper and lower tooth surfaces to form an exactly matching mouth guard.

The putty mass 20 takes approximately three to five minutes to set. In order to gauge the setting process, a small portion of the putty mass 44 can be separated from the amalgamated putty mass before it is formed into a sausage-like roll. The separated portion is then occasionally tested by the person making the mouth guard. By pressing a small portion of amalgamated material, the person making the mouth guard can gauge the progress of the catalytic setting reaction. Between gauging the progress of the reaction by timing it against a clock and directly monitoring the reaction by inspection of a sample, the curing, or setting, of the putty mass 20 can be gauged with some degree of accuracy.

Figure 7A:
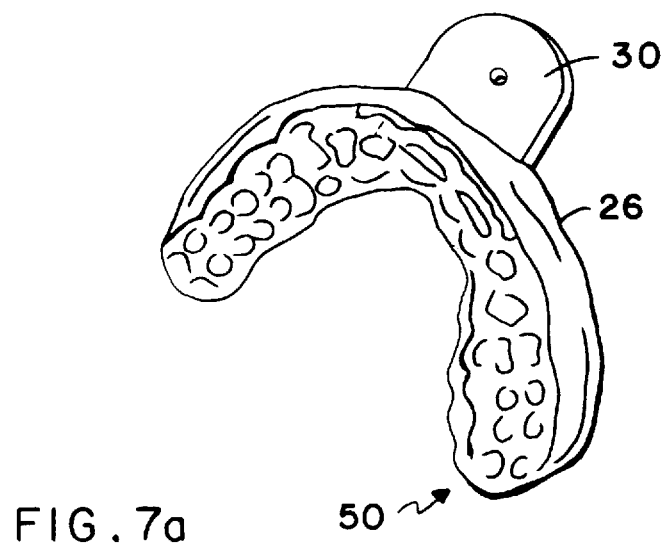
FIG. 7a shows the recently formed mouthpiece with the bite bar still inserted.
Figure 7B:
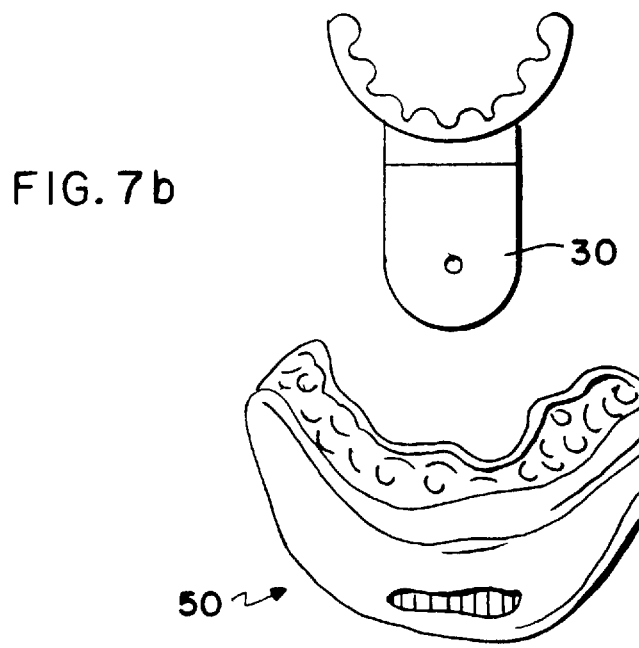
FIG. 7b shows the recently formed mouth guard with the bite bar removed.

Generally, the putty mass 20 does not stick, or adhere, to the mouth-guard maker's teeth; so it is generally easily extracted from between the teeth and from the mouth of the person making the mouth guard. Once the putty mass has sufficiently set, the assembly is removed from the mouth, and the bite bar 30 is removed from the putty mass 20. FIG. 7a shows the now-formed mouth guard 50 as recently removed from the mouth. FIG. 7b shows the bite bar being retracted from the concave portion of the now-formed mouth guard 50.

Figure 8:
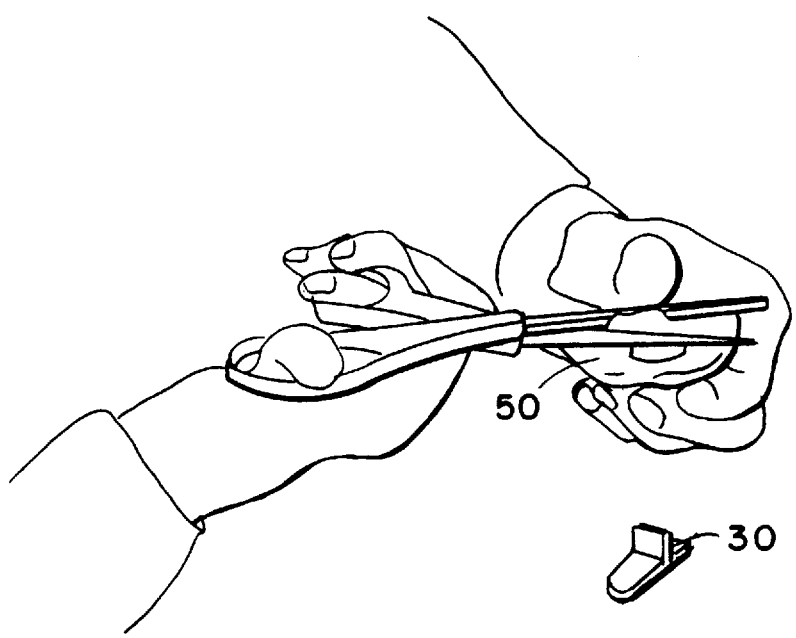
FIG. 8 shows the cutting of extraneous hardened putty matter from the forming mouth guard.

To remove the bite bar 30 from the putty mass 20, the handle may be pressed into the now-formed mouth guard to eject the bite bar. The handle 32 slips through the aperture formed in the putty mass 20 and may be further pulled from the putty mass by holding the putty mass 20 in place and pulling on the shield or prongs 34, 36, 38. Likewise, the handle may be pushed into the putty mass 20. As the now-formed mouth guard 50 continues to set, extra material may be cut away from the mouth guard 50 by using scissors or the like (FIG. 8).

Figure 9:
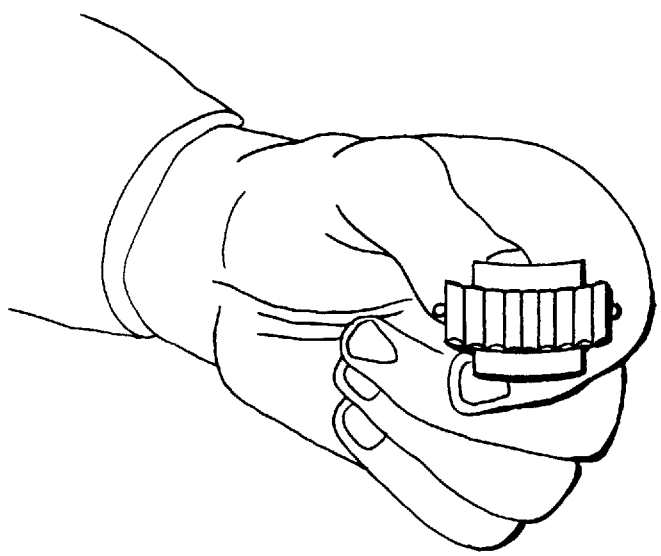
FIG. 9 shows a portion of the bite bar that is disposed to the wearer's mouth when the putty mass with bite bar is inserted into the mouth.
Figure 10:
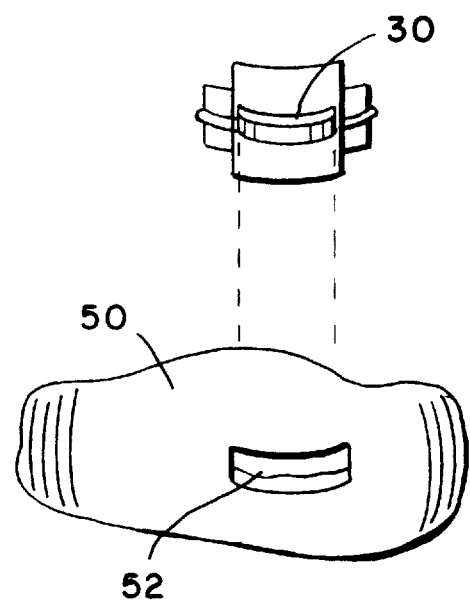
FIG. 10 shows an exterior view of the impressed putty mass forming the mouth guard and a head-on view of the handle of the bite bar.

Once the extraneous material has been cut away from the mouth guard, the catalytic reaction continues until complete, forming a somewhat pliable but generally very resilient mouth guard for use in rough sports and the like. The storage box 12 may then be used to hold the mouth guard 50 when not in use. As a part of the kit, additional putty materials may be supplied so that additional mouth guards may be made as needed. FIG. 9 shows a face-on view of the bite bar 30 as viewed looking at the prongs 36, 38 and shield 34. FIG. 10 shows a face-on view of the bite bar 30 as viewed from the handle 32. The aperture formed in the mouth guard 50 is shown immediately below the bite bar 30. The mouth guard 50 is defined in a central aperture 52 which may be used for breathing and which is formed by the bite bar 30 during the mouth-guard-making process.

Figure 11:
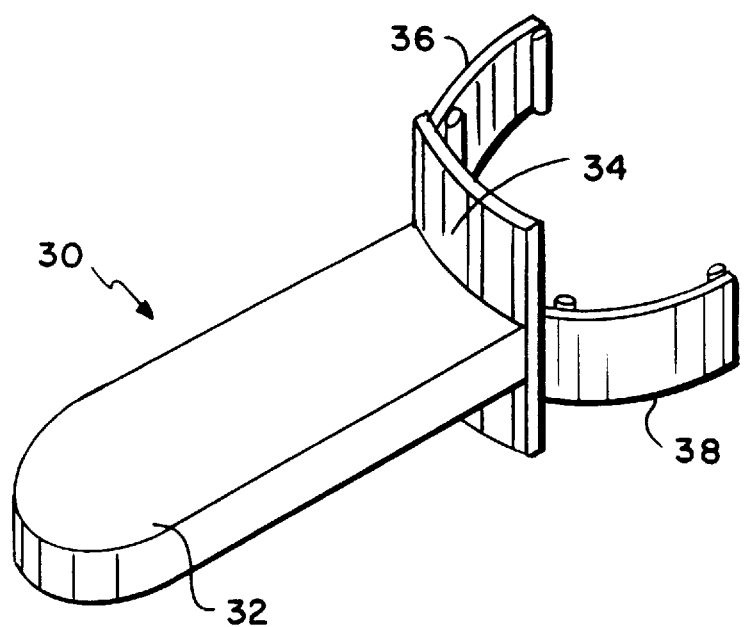
FIG. 11 shows a perspective view of the bite bar of the present invention.

FIG. 11 shows a rear perspective view of the bite bar 30 of the present invention. The handle 32 projects perpendicularly from a shield 34 and provides means for forming the aperture 52 and the mouth guard 50 as well as providing a handle for easily holding the putty-mass 20 and bite-bar 30 assembly during the mouth-guard-making process. Left prong 36 and right prong 38 curve away from the shield 34 and the handle 32, generally in the plane of the handle 32. The prongs 36, 38 are vertically extended in the plane of the shield 34 so as to provide a supporting surface for the putty mass 20. The curvature of the prongs 36, 38 is such as to allow the adjacent putty mass 20 to curve in an anatomically conforming way. By following the curvature of the prongs 36, 38, the ends 24 of the putty mass 20 generally fit between the occluding surfaces of the upper and lower teeth. This places the putty mass 20 in excellent position for taking a dental impression and forming the mouth guard 50.

Figure 12:
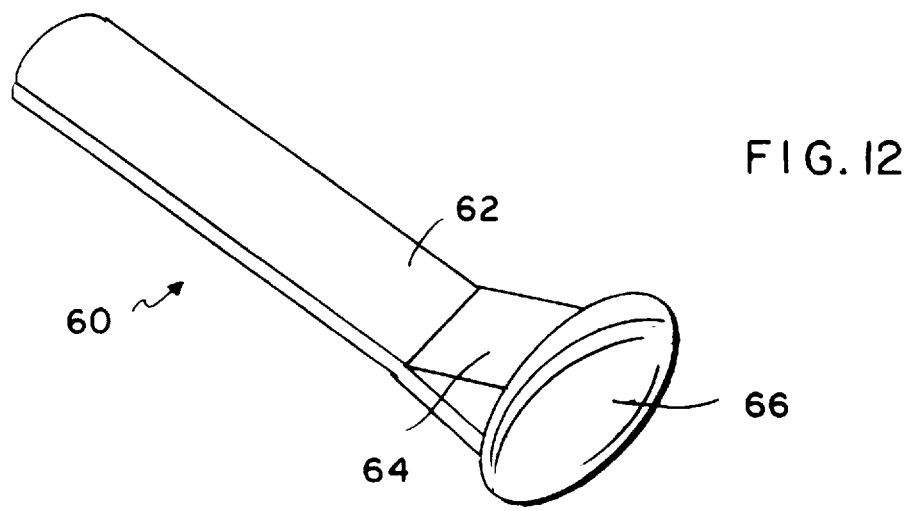
FIG. 12 shows a front perspective view of a preferred bite bar of the present invention.
Figure 13:
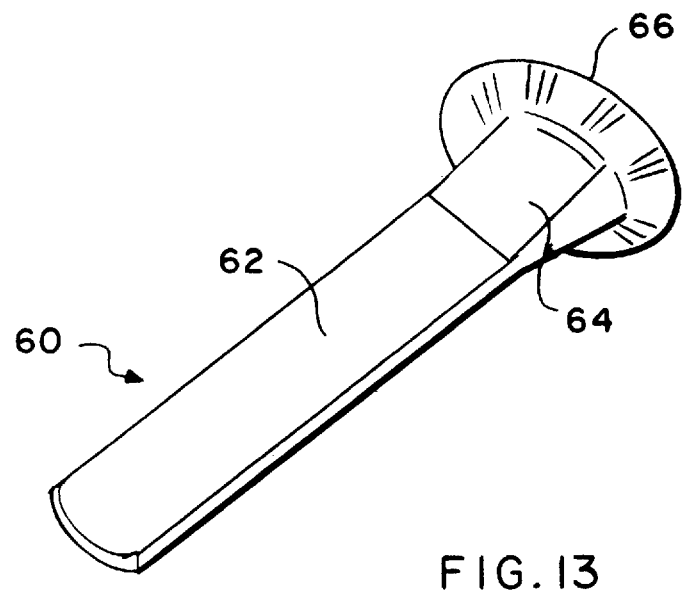
FIG. 13 shows a rear perspective view of a preferred bite bar of the present invention.

In FIGS. 12 and 13, a preferred bite bar embodiment 60 has a handle 62 that leads into a flared supporting brace 64. The flared supporting brace 64 emerges from a distal end of the handle to provide a greater surface area to which an integral concave shield 66 may be attached. The integral concave shield performs several tasks, including combining into one integral structure the shield 34 and prongs 36 and 38 as shown in the embodiment portrayed in FIG. 11. The concave surface of the integral concave shield 66 conforms with the interior of the mouth so as to provide better means by which the putty mass 20 may be supported and formed around the concave shield 66. While the shield 34 shown in FIG. 11 is horizontally concave, the integral concave shield 66 of FIGS. 12 and 13 is concave in both the vertical and horizontal directions.

The preferred bite bar 60 is approximately three inches in length with the handle 62 being approximately a half inch wide and a quarter inch high. The integral concave shield 66 is approximately one inch high and an inch and a half wide. These measurements are approximate and may be adjusted for persons with mouths of different sizes. For example, a bite bar to form a mouth guard for a child may be of a different and smaller size than that used for an adult.

Advantages achieved by use of the preferred bite bar 60 not only include the mouth-interior-conforming concave surface 66 but also the flared supporting brace 64 and the handle 62 that form a larger breathing hole to enable easier breathing and almost discernable speech when the mouth guard is placed in the mouth. The preferred bite bar 60 also has no undercut so that the center piece, or handle, 60 pulls out very easily once the mouth guard has set. When the putty mass 20 is pierced by the handle 62 and formed about the integral concave shield 66, the convex surface 68 provides an excellent template upon which the putty mass 20 may be molded to conform to the opposing occlusion surfaces of the teeth.

With respect to both illustrated embodiments of the bite bar shown in FIGS. 11–13, once such bite bars are used, the teeth do not touch each other when they bite into the putty mass thereby making the mouth guard stronger than if the teeth were able to contact one another during the molding process.

While polyvinyl siloxane materials are generally known in the art in both base and catalytic forms, other substances forming sufficiently viscous and self-hardening impression means may also be advantageously used in the present inventive method. While the present invention has been described with regards to particular embodiments, it is recognized that additional variations of the present invention may be devised without departing from the inventive concept.

What we claim is:

1. A method for making a mouth guard, the steps comprising:

providing viscous and self-hardening means by which to form a dental impression;

forming said viscous means into a generally cylindrical shape for easy insertion into a person's mouth;

providing a bite bar for manipulation and support of said viscous means;

inserting said bite bar into said viscous means to form a mouth-guard assembly;

forming said viscous means about said bite bar so that said viscous means generally fits between dental-occlusion surfaces of said person's mouth;

inserting said mouth-guard assembly into said mouth and biting into said viscous means;

allowing said assembly to remain in said mouth until said viscous means sets sufficiently to retain said dental impression of said person thereby forming the mouth guard;

removing said assembly from said mouth; and removing said bite bar from said viscous means to form a ventilation aperture in the mouth guard.

2. The method for making a mouth guard as set forth in claim 1, wherein said step of providing said viscous means further comprises:

providing a base putty of polyvinyl siloxane;

providing a catalyst putty of polyvinyl siloxane; and mixing said base putty with said catalyst putty to form said viscous and self-hardening means.

3. The method for making a mouth guard as set forth in claim 2, wherein said base putty and said catalyst putty are mixed in approximately equal amounts.

4. The method for making a mouth guard as set forth in claim 3 wherein said approximately equal amounts are approximately seven and one-half milliliters (7½ ml).

5. The method for making a mouth guard as set forth in claim 2, wherein said base putty and said catalyst putty are different colors and thorough mixing of said putties may be generally determined when said viscous means has a uniform color.

6. The method for making a mouth guard as set forth in claim 1, wherein said step for forming said viscous means in a generally cylindrical shape further comprises:

forming said viscous means into a shape of approximately three inches (3 in.) in length with a center diameter of approximately one inch (1 in.) and end diameters of approximately one-half inch (½ in.).

7. The method for making a mouth guard as set forth in claim 1, wherein the step of providing a bite bar comprises providing a bite bar comprising:

a handle, said handle of sufficient length to project through said viscous means to form said ventilation aperture and to project past said viscous means to provide grasping means by which said person may manipulate said mouth-guard assembly without touching said viscous means; and a shield, said shield coupled to said handle and obstructing passage of said handle through said viscous means.

8. The method for making a mouth guard as set forth in claim 7, wherein the step of providing a bite bar further comprises:

providing a bite bar having opposing first and second prongs coupled to said shield, said first and second prongs curving away from said handle on either side of said shield, said first and second prongs curving away from said shield in a manner so that when said viscous means is formed about said bite bar, said viscous means attains a curved shape generally fitting between said dental-occlusion surfaces.

9. The method for making a mouth guard as set forth in claim 7, wherein the step of providing a bite bar further comprises:

providing a bite bar wherein said shield conforms to the interior of said mouth, said shield having a first convex side coupled to said handle and a second concave side, said first convex side curving away from said handle in a manner so that when said viscous means is formed about said bite bar, said viscous means attains a curved shape generally fitting between said dental-occlusion surface.

10. The method for making a mouth guard as set forth in claim 7, wherein the step of inserting said bite bar into said viscous means further comprises:

inserting said handle into a central portion of said viscous means until said viscous means engages said shield.

11. The method for making a mouth guard as set forth in claim 10, wherein the step of forming said viscous means about said bite bar comprises pressing said viscous means to curvedly conform to exterior surfaces of said shield.

12. The method for making a mouth guard as set forth in claim 11, wherein the step of removing said bite bar from said viscous means, further comprises:

disengaging said bite bar from the mouth guard by moving said handle through the mouth guard in a direction toward said shield.

13. The method for making a mouth guard as set forth in claim 1, wherein said step of allowing said assembly to remain in said mouth until said viscous means sets sufficiently, further comprises:

allowing said assembly to remain in said mouth approximately three to five minutes (3–5 min.) while said viscous means sets; and monitoring setting progress of a sample of said viscous means not formed about said bite bar, said sample generally setting at the same rate as said viscous means formed about said bite bar.

14. A method for making a mouth guard, the steps comprising:

providing a base putty of polyvinyl siloxane;

providing a catalyst putty of polyvinyl siloxane;

mixing said base putty with said catalyst putty in approximately equal amounts of approximately seven and one-half milliliters (7½ ml) to form a viscous and self-hardening means by which to form a dental impression, said base putty and said catalyst putty being different colors and thorough mixing of said putties generally determined when said viscous means attains a uniform color;

forming said viscous means into a generally cylindrical shape having a generally cylindrical shape of approximately three inches (3 in.) in length with a center diameter of approximately one inch (1 in.) and end diameters of approximately one-half inch (½ in.) for easy insertion into a person's mouth;

providing a bite bar for manipulation and support of said viscous means, said bite bar comprising:
   a handle, said handle projecting through and past said viscous means to provide grasping means by which said person may manipulate said mouth-guard assembly without touching said viscous means; and
   a shield, said shield coupled to said handle and obstructing passage of said handle through said viscous means;

inserting said handle into a central portion of said viscous means until said viscous means engages said shield to form a mouth-guard assembly;

forming said viscous means about said bite bar by pressing said viscous means to curvedly conform to exterior surfaces of said shield so that said viscous means generally fits between said dental-occlusion surfaces of said person's mouth;

inserting said mouth-guard assembly into said mouth and biting into said viscous means;

allowing said assembly to remain in said mouth until said viscous means sets sufficiently to retain the dental impression of said person thereby forming the mouth guard by allowing said assembly to remain in said mouth approximately three to five minutes (3–5 min.) while said viscous means sets and by monitoring setting progress of a sample of said viscous means not formed about said bite bar, said sample generally setting at the same rate as said viscous means formed about said bite bar;

removing said assembly from said mouth; and removing said bite bar from said viscous means by disengaging said bite bar from the mouth guard by moving said handle through the mouth guard in a direction toward said shield to form a ventilation aperture in the mouth guard.

15. The method for making a mouth guard as set forth in claim 14, wherein the step of providing a bite bar further comprises:
   providing a bite bar having opposing first and second prongs coupled to said shield, said first and second prongs curving away from said handle on either side of said shield, said first and second prongs curving away from said shield in a manner so that when said viscous means is formed about said bite bar, said viscous means attains a curved shape generally fitting between said dental-occlusion surfaces.

16. The method for making a mouth guard as set forth in claim 14, wherein the step of providing a bite bar further comprises:
   providing a bite bar wherein said shield conforms to the interior of said mouth, said shield having a first convex side coupled to said handle and a second concave side, said first convex side curving away from said handle in a manner so that when said viscous means is formed about said bite bar, said viscous means attains a curved shape generally fitting between said dental-occlusion surface.

17. The method for making a mouth guard as set forth in claim 16, wherein the step of providing a bite bar further comprises:
   providing a bite bar having opposing first and second prongs coupled to said shield, said first and second prongs curving away from said handle on either side of said shield, said first and second prongs curving away from said shield in a manner so that when said viscous means is formed about said bite bar, said viscous means attains a curved shape generally fitting between said dental-occlusion surfaces.

18. The method for making a mouth guard as set forth in claim 14, wherein the step of providing a bite bar further comprises:
   providing a bite bar wherein said shield conforms to the interior of said mouth, said shield having a first convex side coupled to said handle and a second concave side, said first convex side curving away from said handle in a manner so that when said viscous means is formed about said bite bar, said viscous means attains a curved shape generally fitting between said dental-occlusion surface.

19. A bite bar for use in forming a mouth guard from a viscous substance, comprising:
   a handle, said handle projecting through and past the viscous substance to provide grasping means by which said person may manipulate the viscous substance without touching the viscous substance;
   a shield, said shield coupled to said handle and obstructing passage of said handle through the viscous substance.

20. The bite bar for use in forming a mouth guard from a viscous substance as set forth in claim 19, wherein the viscous substance comprises:
   a base putty of polyvinyl siloxane;
   a catalyst putty of polyvinyl siloxane;
   mixing said base putty with said catalyst putty in approximately equal amounts of approximately seven and one-half milliliters (7½ ml) to form the viscous substance by which to form a dental impression, said base putty and said catalyst putty being different colors and thorough mixing of said putties generally determined when the viscous substance attains a uniform color.

21. The bite bar for use in forming a mouth guard from a viscous substance as set forth in claim 20, wherein the viscous substance is formed into a generally cylindrical shape having a generally cylindrical shape of approximately three inches (3 in.) in length with a center diameter of approximately one inch (1 in.) and end diameters of approximately one-half inch (½ in.) for easy insertion into a person's mouth.

22. The bite bar for use in forming a mouth guard from a viscous substance as set forth in claim 21 wherein said handle is inserted into a central portion of the viscous substance until the viscous substance engages said shield to form a mouth-guard assembly.

23. The bite bar for use in forming a mouth guard from a viscous substance as set forth in claim 22, wherein the viscous substance is formed about the bite bar by pressing the viscous substance to curvedly conform to exterior surfaces of said shield so that the viscous substance generally fits between said dental-occlusion surfaces of said person's mouth.

24. The bite bar for use in forming a mouth guard from a viscous substance as set forth in claim 23, wherein:
   said mouth-guard assembly is inserted into said mouth and the viscous substance is bitten into to form said dental impression; and said assembly is allowed to remain in said mouth until the viscous substance sets sufficiently to retain said dental impression of said person thereby forming the mouth guard by allowing said assembly to remain in said mouth approximately three to five minutes (3–5 min.) while the viscous substance sets and by monitoring setting progress of a sample of the viscous substance not formed about the bite bar, said sample generally setting at the same rate as the viscous substance formed about the bite bar.

25. The bite bar for use in forming a mouth guard from a viscous substance as set forth in claim 24, wherein
said assembly is removed from said mouth; and
the bite bar is removed from the viscous substance by disengaging the bite bar from the mouth guard by moving said handle through the mouth guard in a direction toward said shield to form a ventilation aperture in the mouth guard.

* * * * *